US00PP37320P2

(12) United States Plant Patent
van Swieten

(10) Patent No.: US PP37,320 P2
(45) Date of Patent: Mar. 10, 2026

(54) ***PHALAENOPSIS* PLANT NAMED 'PHA329495'**

(50) Latin Name: *Phalaenopsis hybrida*
Varietal Denomination: PHA329495

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/329,242

(22) Filed: Sep. 15, 2025

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
See application file for complete search history.

(56) References Cited

U.S. PATENT DOCUMENTS

PP28,944 P2 * 2/2018 Van Swieten ..... A01H 6/62
Plt./311

* cited by examiner

*Primary Examiner* — Susan Mccormick Ewoldt
(74) *Attorney, Agent, or Firm* — C. Anne Whealy

(57) ABSTRACT

A new and distinct cultivar of *Phalaenopsis* plant named 'PHA329495', characterized by its upright plant habit; medium to tall in height; moderately vigorous growth habit and moderate growth rate; strong flowering stems; freely flowering habit with typically two inflorescences developing per plant, each inflorescence with numerous flowers; medium to broad white-colored flowers; and good postproduction longevity.

2 Drawing Sheets

Figure 1:
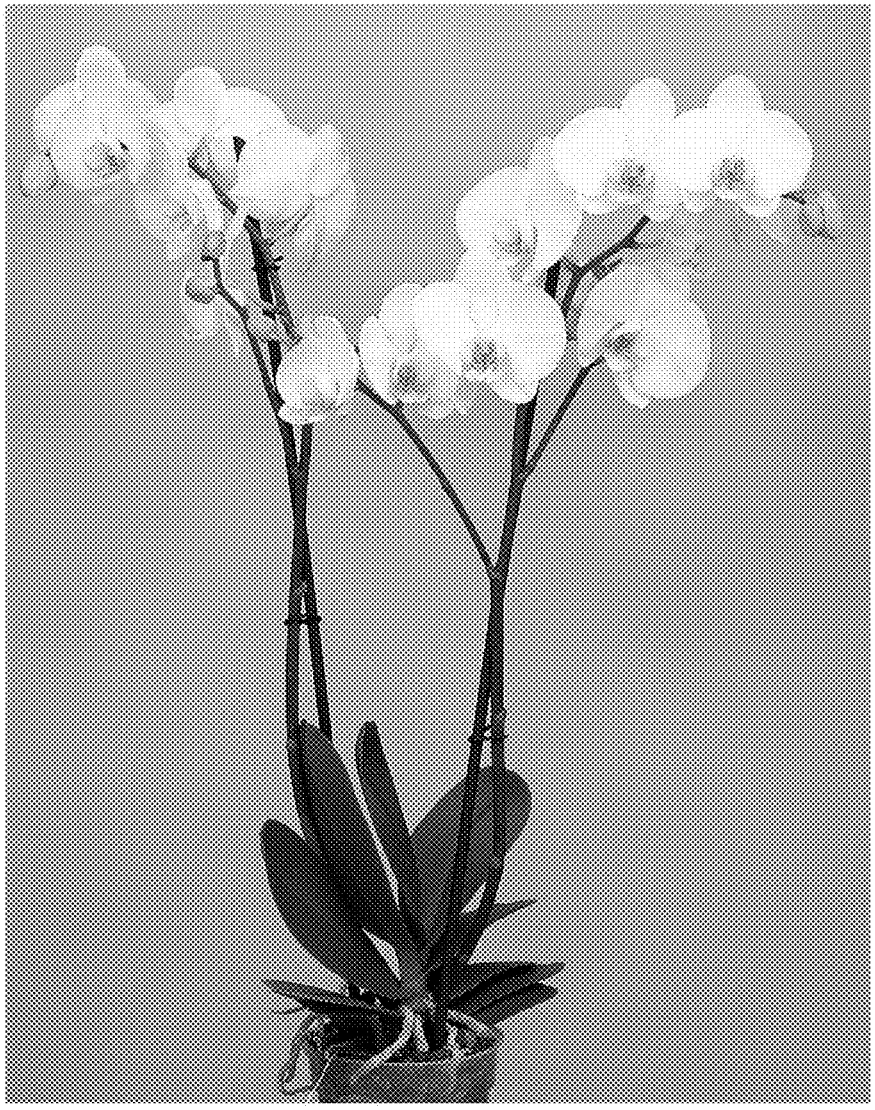

Botanical designation: *Phalaenopsis hybrida.*
Cultivar denomination: 'PHA329495'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, Anthura B.V. of Bleiswijk, The Netherlands on Aug. 14, 2024, application number 2024/1901. Foreign priority is not claimed to this application.

BACKGROUND OF THE INVENTION

The present invention relates to a new and distinct cultivar of *Phalaenopsis* plant, botanically known as *Phalaenopsis hybrida*, commonly referred to as a *Phalaenopsis* or Moth Orchid and hereinafter referred to by the name 'PHA329495'.

The new *Phalaenopsis* plant is a product of a planned breeding program conducted by the Inventor in Bleiswijk, The Netherlands. The objective of the breeding program is to develop new freely flowering *Phalaenopsis* plants with white-colored flowers.

The new *Phalaenopsis* plant originated from a cross-pollination in September 2017 in Bleiswijk, The Netherlands of a proprietary breeding selection of *Phalaenopsis hybrida* identified as code number 12-053497-0001, not patented, as the female, or seed, parent with *Phalaenopsis hybrida* 'PHALCARDOK', disclosed in U.S. Plant Pat. No. 25,447, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in June 2020.

Asexual reproduction of the new *Phalaenopsis* plant by in vitro meristem propagation in a controlled environment in Bleiswijk, The Netherlands since June 2020 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA329495'. These characteristics in combination distinguish 'PHA329495' as a new and distinct *Phalaenopsis* plant:

1. Upright plant habit; medium to tall in height.
2. Moderately vigorous growth habit and moderate growth rate.
3. Strong flowering stems.
4. Freely flowering habit with typically two inflorescences developing per plant, each inflorescence with numerous flowers.
5. Medium to broad white-colored flowers.
6. Good postproduction longevity.

Plants of the new *Phalaenopsis* can be compared to plants of the female parent selection. Plants of the new *Phalaen-*

*opsis* differ primarily from plants of the female parent selection in the following characteristics:

1. Leaves of plants of the new *Phalaenopsis* are more elongated than leaves of plants of the female parent selection.
2. Flowers of plants of the new *Phalaenopsis* are flat in lateral view whereas flowers of plants of the female parent selection are concave in lateral view.
3. Petal apices of plants of the new *Phalaenopsis* are obtuse whereas petal apices of plants of the female parent selection are emarginate.

Plants of the new *Phalaenopsis* can be compared to plants of the male parent, 'PHALCARDOK'. Plants of the new *Phalaenopsis* differ primarily from plants of 'PHALCARDOK' in the following characteristics:

1. Leaves of plants of the new *Phalaenopsis* are semi-erect to horizontal in aspect whereas leaves of plants of 'PHALCARDOK' are semi-erect in aspect.
2. Leaf apices of plants of the new *Phalaenopsis* are obtuse to rounded whereas leaf apices of plants of 'PHALCARDOK' are acute.
3. Flowers of plants of the new *Phalaenopsis* are not as broad as flowers of plants of 'PHALCARDOK'.

Plants of the new *Phalaenopsis* can be compared to plants of *Phalaenopsis* hybrida 'PHALFOREI', disclosed in U.S. Plant Pat. No. 28,944. In side-by-side comparisons, plants of the new *Phalaenopsis* differ primarily from plants of 'PHALFOREI' in the following characteristics:

1. Plants of the new *Phalaenopsis* are shorter than plants of 'PHALFOREI'.
2. Leaves of plants of the new *Phalaenopsis* are not as elongated as leaves of plants of 'PHALFOREI'.
3. Flower petals of plants of the new *Phalaenopsis* are free whereas flower petals of plants of 'PHALFOREI' are not free and are "touching".
4. The lateral lobes of the labella of plants of the new *Phalaenopsis* are not as inwardly curved as the lateral lobes of the labella of plants of 'PHALFOREI'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA329495' grown in a container.

Figure 2:
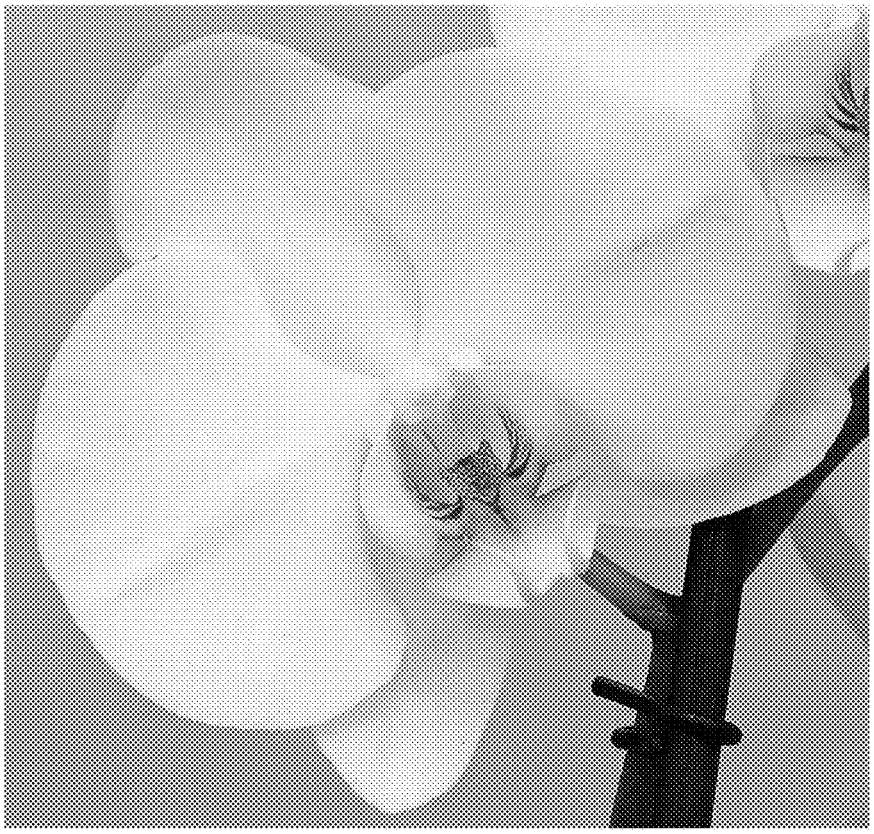

The photograph on the second sheet (FIG. 2) is a close-up view of a typical flower of 'PHA329495'.

DETAILED BOTANICAL DESCRIPTION

The aforementioned photographs and following observations and measurements describe plants grown during the winter and early spring in 12-cm containers in a glass-covered greenhouse in Bleiswijk, The Netherlands and grown under cultural practices typically used in commercial *Phalaenopsis* production. Plants were 18 months old when the photographs and description were taken. During the first 14 months of production of the plants, day and night temperatures averaged 28.5° C., and during the last four months of production of the plants, day and night temperatures averaged 20° C. Throughout the production of the plants, light levels ranged from 100 μmol to 180 μmol. In the following description, color references are made to The Royal Horticultural Society Colour Chart, 2015 Edition, except where general terms of ordinary dictionary significance are used.

Botanical classification: *Phalaenopsis hybrida* 'PHA329495'.

Parentage:

*Female, or seed, parent*.—Proprietary breeding selection of *Phalaenopsis hybrida* identified as code number 12-053497-0001, not patented.

*Male, or pollen, parent*.—*Phalaenopsis hybrida* 'PHALCARDOK', disclosed in U.S. Plant Pat. No. 25,447.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically light green in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; upright plant habit; medium to tall in height; typically two inflorescences developing per plant, each inflorescence with numerous flowers; monopodial; moderately vigorous growth habit and moderate growth rate.

*Plant height, substrate level to top of foliar plane*.—About 17.2 cm.

*Plant height, substrate level to top of floral plane*.—About 55 cm.

*Plant diameter or spread*.—About 35.9 cm.

Leaf description:

*Arrangement and quantity*.—Distichous, simple; sessile; about six to eight fully-developed leaves per plant.

*Length*.—About 15.8 cm.

*Width*.—About 7.3 cm.

*Aspect*.—Semi-erect to horizontal.

*Shape*.—Obovate to elliptic-obovate; slightly carinate; slightly curled upwards at the apex.

*Apex*.—Unequal obtuse to unequal rounded.

*Base*.—Sheathing. Sheath length: About 1.9 cm. Sheath width: About 1.3 cm. Sheath color: Close to 143C.

*Margin*.—Entire; not undulate.

*Texture and luster, upper and lower surfaces*.—Smooth, glabrous; slightly glossy.

*Venation pattern*.—Camptodromous.

*Color*.—Developing leaves, upper surface: Close to NN137B; narrow marginal edges, close to 151A. Developing leaves, lower surface: Close to 146B; narrow marginal edges, close to 151A. Fully expanded leaves, upper surface: Close to NN137A and NN137B; narrow marginal edges, close to 143C; venation, close to 139A. Fully expanded leaves, lower surface: Close to 146B; narrow marginal edges, close to 151A; venation, close to 143B to 143C.

Inflorescence description:

*Appearance and flowering habit*.—Showy zygomorphic flowers arranged on axillary simple or branched racemes; typically two inflorescences develop per plant; each inflorescence with about 15 flowers; flowers face outwardly on upright to outwardly arching inflorescences supported by upright peduncles; flowers with three petals, two lateral petals and one center petal transformed into a labellum and three sepals.

*Fragrance*.—None detected.

*Time to flower*.—Plants begin flowering about four months after planting; plants flower naturally during the winter into the spring.

*Flower longevity*.—Long flowering period, individual inflorescences maintain good substance for about 21 weeks on the plant; flowers not persistent.

*Inflorescence length* (*lowermost flower to inflorescence apex*).—About 29.6 cm.

*Inflorescence width*.—About 20.5 cm.

*Flower buds*.—Height: About 1.9 cm. Diameter: About 1.4 cm by 1.6 cm. Shape: Broadly ovate. Color: Close to a blend of 145A and 149A.

*Flower size*.—About 9.5 cm (vertical) by 10 cm (horizontal).

*Flower depth*.—About 3.4 cm.

*Petals, quantity and arrangement*.—Three, two lateral petals and one center petal transformed into a labellum.

*Lateral petals*.—Length: About 4.6 cm. Width: About 5.5 cm. Shape: Broadly reniform to close to lunate. Apex: Obtuse. Margin: Entire; not undulate. Texture and luster, upper and lower surfaces: Smooth, glabrous; moderately velvety; matte. Color: When opening, upper surface: Close to NN155C and NN155D. When opening, lower surface: Close to 155C; towards the margins, close to NN155D. Fully opened, upper surface: Close to NN155D; color does not change with subsequent development. Fully opened, lower surface: Close to NN155D; towards the base, close to NN155B; colors do not change with subsequent development.

*Labella*.—Appearance: Three-parted with two lateral lobes and a central lobe; overall shape, broadly cordate. Length, lateral lobes: About 2.2 cm. Width, lateral lobes: About 1.7 cm. Length, central lobe: About 2.4 cm. Width, central lobe: About 7 mm to 25 mm. Length, cirrhose tips: About 2 cm. Shape, lateral lobes: Obovate. Shape, central lobe: Kite-shaped with an elongated apex. Apex, lateral lobes: Obtuse. Apex, central lobe: Narrowly acute with two cirrhose apices, curled and pointing upwards and backwards. Margins, lateral and central lobes: Entire. Texture and luster, lateral and central lobes, upper and lower surfaces: Smooth, glabrous; velvety; matte. Callosities: Located at the base of the labellum and attachment point of the lateral petals; about 5 mm in length, about 6 mm in width and about 6 mm in height. Color: When opening, upper surface: Lateral lobes: Close to NN155D; towards the base, close to 155C; at the base, axial stripes, close to 182A and 182B; lower margins, close to 1A. Central lobe: Close to NN155C; towards the base, close to 154B; at the base, close to NN155A with radial stripes, close to 184B; narrow distal margins, close to N170A; cirrhose apices, close to 154C. Callosities: Close to 1B, 1C and 155A; towards the apex, close to 14B with fine dots, close to 185B. When opening, lower surface: Lateral lobes: Close to NN155D; towards the base, close to 155C and 157D; lower margins, close to 1A. Central lobe: Close to NN155B; towards the base, close to 154B; at the base, close to 157D; narrow distal margins, close to N170A; cirrhose apices, close to 154C. Fully opened, upper surface: Lateral lobes: Close to NN155D; at the base, axial stripes, close to 182A and 182B; lower margins, close to 2B. Central lobe: Close to NN155D; towards the base, close to 154C; at the base, close to NN155A with radial stripes, close to 181B; narrow distal margins, close to N170A and N170B; cirrhose apices, close to 154C. Callosities: Close to 12C; towards the apex, close to 15A; fine dots, close to 185A. Fully opened, lower surface: Lateral lobes: Close to NN155D; lower margins, close to 6C. Central lobe: Close to NN155D; towards the base, close to 154C; at the base, close to 155C; narrow distal margins, close to N170A and N170B; cirrhose apices, close to 154C.

*Sepals*.—Quantity and arrangement: Three, one upper dorsal sepal and two lower lateral sepals. Length, dorsal sepal: About 4.7 cm. Width, dorsal sepal: About 3.3 cm. Length, lateral sepals: About 4.9 cm. Width, lateral sepals: About 2.9 cm. Shape, dorsal sepal: Elliptic-oblong. Shape, lateral sepals: Ovate. Apex, dorsal sepal: Shallowly retuse. Apex, lateral sepals: Bluntly acute. Base, dorsal and lateral sepals: Cuneate. Margins, dorsal and lateral sepals: Entire; not undulate. Texture and luster, dorsal and lateral sepals, upper and lower surfaces: Smooth, glabrous; moderately velvety; matte. Color, dorsal sepal: When opening, upper surface: Close to NN155B. When opening, lower surface: Close to 150D; towards the apex and margins, close to 155C tinged with close to N155B. Fully opened, upper surface: Close to NN155C; towards the apex and margins, close to NN155D. Fully opened, lower surface: Close to 155A slightly tinged with close to 76B; apical margins, close to NN155D. Color, lateral sepals: When opening, upper surface: Close to 157D; towards the base, close to a blend of 145D and 157A. When opening, lower surface: Distally, close to 154D; proximally, close to 155C tinged with close to N155B. Fully opened, upper surface: Close to 155C; towards the base, close to 150D. Fully opened, lower surface: Close to 150D; venation, close to 154D.

*Peduncles*.—Length: About 55.3 cm. Diameter: About 7 mm. Strength: Strong. Aspect: Upright to outwardly arching. Texture and luster: Smooth, glabrous; matte. Color: Close to N189D; densely covered with fine dots and marbling, close to 147C.

*Pedicels*.—Length: About 4.2 cm. Diameter: About 3 mm. Strength: Moderately strong. Aspect: About 60° from peduncle axis. Texture and luster: Smooth, glabrous; matte. Color: Close to 145A and 145B; distal end, close to 159B; proximal end, close to 148A.

*Reproductive organs*.—Androecium: Column length: About 9 mm. Column width: About 6 mm. Column color: Close to NN155C. Pollinia quantity: Two. Pollinia diameter (per two pollinia): About 2.5 mm. Pollinia color: Close to 23A. Gynoecium: Stigma length: About 4 mm. Stigma width: About 5 mm. Stigma shape: Reniform. Stigma color: Close to 157D. Ovary length: About 8 mm. Ovary diameter: About 1 mm. Ovary color: Close to 150A. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA329495' as herein illustrated and described.

* * * * *